US00PP12469P2

(12) United States Plant Patent
Meerow

(10) Patent No.: US PP12,469 P2
(45) Date of Patent: Mar. 19, 2002

(54) AMARYLLIS PLANT NAMED 'BAHIA'

(75) Inventor: Alan Meerow, Davie, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 09/396,482

(22) Filed: Sep. 15, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Wendy C Baker
(74) *Attorney, Agent, or Firm*—C. A. Whealy

(57) ABSTRACT

A distinct cultivar of Amaryllis plant named 'Bahia', characterized by its unique red and white picotee flowers that appear luminous and crystalline; resistance to Red Scorch Fungus; and excellent high temperature tolerance.

1 Drawing Sheet

BACKGROUND OF THE INVENTION

The present invention relates to a new and distinct cultivar of Amaryllis plant, botanically known as Hippeastrum hybrid and referred to by the cultivar name Bahia.

The new cultivar is a product of a planned breeding program conducted by the Inventor in Fort Lauderdale, Fla. The objective of the breeding program is to develop new Amaryllis cultivars with novel flower coloration patterns.

The new Amaryllis originated from a cross made by the Inventor in Fort Lauderdale, Fla., of a proprietary selection of the interspecific cross *Hippeastrum pardinum*×*Hippeastrum papilio* identified as code number H-8-14 (not patented), as the female, or seed, parent with the Hippeastrum hybrid cultivar White Christmas (not patented), as the male, or pollen, parent.

The cultivar Bahia was discovered and selected by the Inventor as a flowering plant within the progeny of the stated cross in a controlled environment in Fort Lauderdale, Fla., in 1994. The selection of this new Amaryllis plant was based on its unique flower coloration pattern.

Plants of the new Amaryllis and plants of the female parent, the interspecific cross identified as H-8-14, differ in flower color and coloration pattern. In addition to flower color, plants of the new Amaryllis are more resistant to Red Scorch Fungus (*Staganospora curtisii*) and more high temperature tolerant than plants of the pure white-flowered male parent, the cultivar White Christmas.

Asexual reproduction of the new cultivar by twin-scale cuttings taken in a controlled environment in Fort Lauderdale, Fla., has shown that the unique features of this new Amaryllis are stable and reproduced true to type in successive generations.

SUMMARY OF THE INVENTION

The cultivar Bahia has not been observed under all possible environmental conditions. The phenotype may vary somewhat with variations in environment such as temperature, daylength and light intensity, without, however, any variance in genotype. The following traits have been repeatedly observed and are determined to be the unique characteristics of 'Bahia'. These characteristics in combination distinguish 'Bahia' as a new and distinct cultivar:

1. Flowers of plants of the new Amaryllis have an unique red and white picotee coloration pattern and appear luminous and crystalline.

2. Plants of the new Amaryllis are resistant to Red Scorch Fungus, *Staganospora curtisii.*

3. Plants of the new Amaryllis have exhibited excellent high temperature tolerance.

The accompanying colored photograph illustrates the overall appearance of the new cultivar, showing the colors as true as it is reasonably possible to obtain in colored reproductions of this type. The photograph comprises a close-up view of typical flowers of 'Bahia'. Flower colors in the photograph may appear different from the actual colors due to light reflectance.

DETAILED BOTANICAL DESCRIPTION

The following observations, measurements and values describe plants of the new cultivar that were about two years old from a bulb scale cutting and grown in Fort Lauderdale, Fla., in a polypropylene-covered shadehouse that provided a 50% reduction in ambient light. During the flowering period, day temperatures ranged from 25 to 30° C. and night temperatures ranged from 15 to 18° C.

Color references are made to The Royal Horticultural Society Colour Chart except where general terms of ordinary dictionary significance are used.

Botanical classification: Hippeastrum hybrid cultivar Bahia.
Parentage:
- *Female or seed parent.*—Proprietary selection of *Hippeastrum pardinum*×*Hippeastrum papilio* identified as code number H-8-14, not patented.
- *Male or pollen parent.*—Hippeastrum hybrid cultivar White Christmas, not patented.

Propagation:
- *Type.*—Twin-scale cuttings.
- *Time to initiate roots, summer.*—About 30 days at temperatures of 30° C.
- *Time to initiate roots, winter.*—About 40 days at temperatures of 22° C.
- *Time to develop roots, summer.*—About 65 days at temperatures of 30° C.

*Time to develop roots, winter.*—About 90 days at temperatures of 22° C.

*Rooting description.*—White; numerous; fine and fibrous to moderately thick and fleshy; freely branching.

Plant description:

*Appearance.*—Perennial herbaceous Amaryllis. Upright and clumping growth habit.

*Crop time.*—From bulb scale cuttings, about two years are required to produce a finished, flowering plant in a 15 to 20-cm container.

*Vigor.*—Moderately vigorous.

*Plant height.*—About 62.5 cm.

*Plant spread.*—About 44 cm.

*Foliage description.*—Arrangement: Distichous, single. Quantity: About 5 per plant. Length, mature leaves: About 51.5 cm. Width, mature leaves: About 4.75 cm. Shape: Lorate. Apex: Acute. Margin: Entire. Texture: Coarse; glabrous. Color: Young foliage, upper surface: 144A. Young foliage, lower surface: 144B. Mature foliage, upper surface: 137B. Mature foliage, lower surface: 137D.

Flower description:

*Appearance.*—Funnel-shaped single flowers arranged in umbels. Corolla and calyx three-parted and fused at the base. Freely flowering, typically about four open flowers per scape and about 10 flowers and flower buds per plant. Flowers last about three or four days. Flowers persistent. Flowers held horizontally, perpendicular to scape.

*Flowering response.*—Plants flower continuously in the spring. Plants typically flower about March 1 to March 15 in Fort Lauderdale, Fla.

*Fragrance.*—Not detected.

*Flower diameter.*—About 17.5 cm.

*Flower depth (height).*—About 17 cm.

*Flower buds.*—Length: About 4 cm. Width: About 1 cm. Shape: Oblanceolate. Color: Towards apex and base, close to 155D; mid-section, 45B. Rate of flower bud opening: About 1 to 2 days.

*Petals.*—Length: About 12 cm. Width: About 5.6 cm. Shape: Elliptic. Apex: Apiculate. Margin: Entire; slightly undulate. Texture: Smooth; petals appear luminous and crystalline. Color: Both surfaces: Ground color, white, close to 155D; overlain with red, 45B, striations along veins and random speckling, 45B; margins, 45B; red fading to 45D with subsequent development.

*Sepals.*—Shape: Elliptic. Apex: Apiculate. Margin: Entire; slightly undulate. Color: Both surfaces: Ground color, white, close to 155D; overlain with red, 45B, striations along veins and random speckling, 45B; margins, 45B; red fading to 45D with subsequent development.

*Scape.*—Length: About 62.5 cm. Diameter: About 1.5 cm. Appearance/aspect: Leafless; upright; not fasciated. Strength: Moderate. Texture: Smooth. Color: 137D.

*Reproductive organs.*—Androecium: Stamen number: Six. Anther shape: Elliptic. Anther size: About 3 to 4 mm. Anther color: White. Pollen amount: Moderate. Pollen color: White. Gynoecium: Pistil number: One. Pistil length: About 12.5 cm. Stigma shape: Trifid. Stigma color: 45B. Style length: About 12.5 cm. Style color: Light red, 45D, and white. Ovary color: 141C.

*Seed.*—Seed development has not been observed.

Bulb description:

*Diameter.*—About 8 cm.

*Circumference.*—About 22 cm.

*Shape.*—Ovoid.

*Color.*—149A; tunic, 165A.

*Offsets produced per year.*—About one offset per bulb.

Disease resistance: Plants of the new Amaryllis have been shown to be resistant to Red Scorch Fungus, *Staganospora curtisii.*

Heat tolerance: Plants of the new Amaryllis have demonstrated good tolerance to high temperatures about 33 to 35° C.

It is claimed:

1. A new and distinct cultivar of Amaryllis plant named 'Bahia', as illustrated and described.

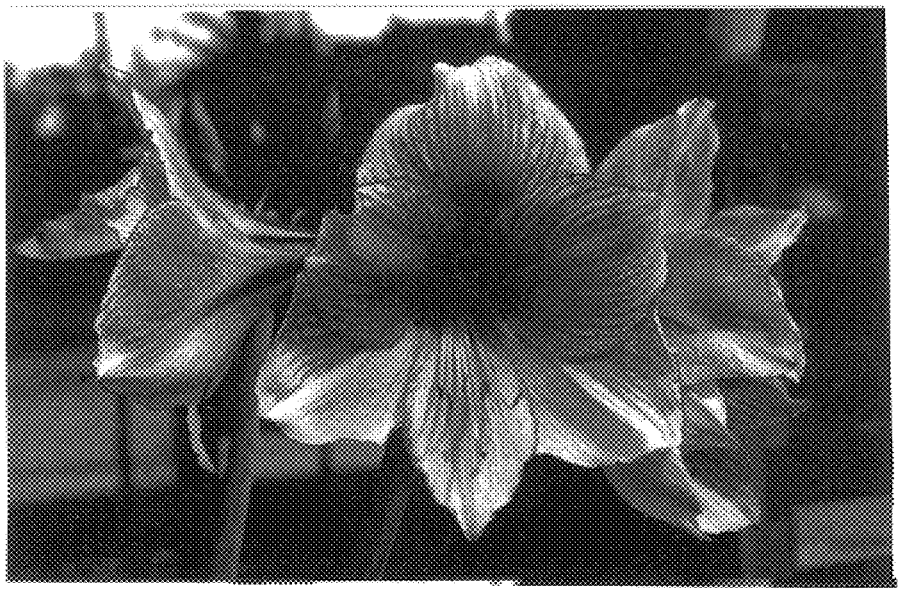

* * * * *